(12) United States Patent
Gohman et al.

(10) Patent No.: US 6,511,696 B2
(45) Date of Patent: Jan. 28, 2003

(54) INFANT FORMULA WITH FREE AMINO ACIDS AND NUCLEOTIDES

(75) Inventors: Sharon Gohman, New Brighton, MN (US); Carol Jo Lowry, Minneapolis, MN (US)

(73) Assignee: Novartis Nutrition AG, Berne (CH)

( * ) Notice: Subject to any disclaimer, the term of this patent is extended or adjusted under 35 U.S.C. 154(b) by 182 days.

(21) Appl. No.: 09/735,884

(22) Filed: Dec. 13, 2000

(65) Prior Publication Data

US 2002/0106436 A1 Aug. 8, 2002

(51) Int. Cl.$^7$ ............... A23L 1/305; A23J 1/00
(52) U.S. Cl. ........... 426/601; 426/656; 426/801; 426/658; 514/45; 514/46
(58) Field of Search ............... 426/656, 801, 426/601, 658, 72, 73; 514/45, 46

(56) References Cited

U.S. PATENT DOCUMENTS

| 4,544,559 A | 10/1985 | Gil et al. | 426/72 |
|---|---|---|---|
| 4,994,442 A | * 2/1991 | Gil et al. | |
| 5,066,500 A | 11/1991 | Gil et al. | 426/72 |
| 5,700,590 A | * 12/1997 | Masor et al. | |
| 5,719,133 A | 2/1998 | Schmidt et al. | 514/58 |
| 5,994,404 A | * 11/1999 | Coupland | |
| 6,077,558 A | * 6/2000 | Euber | |

FOREIGN PATENT DOCUMENTS

| AU | 200022638 | 3/2000 |
|---|---|---|
| EP | 0 302 807 B1 | 1/1994 |

* cited by examiner

Primary Examiner—Anthony J. Weier
(74) Attorney, Agent, or Firm—John W. Kung

(57) ABSTRACT

A fat-rich powder provides the complete nutritional needs of an at-risk infant no more than one year old, who has acquired a milk allergy, such as cow's milk allergy ("CMA"), and/or an allergy to protein in "soy milk", as well as digestive or absorption problems resulting in a damaged gut. Because such an infant must derive all its protein from amino acids it is not fed any ingredient derived from mammalian milk, but a combination of amino acids with nucleotides in specified amounts along with free L-glutamine, maintaining specified ratios of their relative amounts, which ratios in the ranges stated are found to be beneficial for healing of the infant's damaged gut, and for promoting cell division to assure its normal growth. A typical feeding of 32.6 gm of the powder delivers 160 cals; the powder, including triglycerides of relatively long chain fatty acids which contribute about 50% of the total caloric content of the powder, is nevertheless solubilized when the powder is manually shaken at 35° C. in a bottle containing 240 ml (8 fl oz) of water.

14 Claims, No Drawings

INFANT FORMULA WITH FREE AMINO ACIDS AND NUCLEOTIDES

BACKGROUND OF THE INVENTION

This invention relates to a non-milk based hypoallergenic infant-formula for "at-risk" infants no more than one year old, who have a documented milk allergy, such as cow's milk allergy ("CMA"), and/or an allergy to protein in "soy milk". By "non-milk based" is meant that no ingredient of the formula is derived from mammalian milk. Because typically, such infants have acquired digestive or absorption problems, the only source of protein in the formula is to be from free amino acids, and the formula is to be storable in powder form but have specified deliverability. By "specified deliverability" is meant that the powder is solubilized in an essentially homogeneous liquid form within less than 30 secs when a unit dosage amount of 32.6 gm of the powder is manually shaken with water at 35° C. in a bottle containing 240 ml (8 fl oz) of water. By "solubilized" is meant that the powder is either soluble in water or forms an emulsion in water forming a liquid having physical characteristics analogous to those of human milk.

Still more particularly, the novel formula of the invention does not otherwise mimic human milk in that nutrient powder contains no intact or antigenic proteins; when the powder is solubilized as a ready-to-feed liquid, it is required to have a viscosity less than 10 cp at 25° C. to allow flow through a tube if the formula is delivered enterally rather than taken orally. By "intact protein" is meant a tripeptide or larger molecule having a molecular weight greater than about 500 Daltons; protein hydrolysates of whey or casein contain a major proportion by weight of tripeptides or larger molecules. Hereafter the term "enterally" specifically refers to feeding through a tube such as is typically inserted into the stomach of an infant who cannot easily be fed orally; and the term "at-risk infant" is used to specify one which is no more than one year old. The age limit is critical because a child more than one year old is not seriously "at-risk" since a one-year old is typically fed other food along with formula, and is relatively tolerant to an unbalanced formula for long enough a time to allow a competent nutritionist to alleviate the effects of the misdirected or misapplied diet. A typical infant, not a prematurely born infant, who is to be fed the novel formula weighs in the range from about 2.3 kg (5 lb) to 5.5 kg (12 lb) at birth, and weighs in the range from about 4.5 kg (10 lb) to 11.5 kg (25 lb) after one year.

The problem is to provide a storable powder formula which (i) provides the entire nutrition requirement of an at-risk infant needing an energy content in the range from about 200–250 Kcal/g nitrogen, without including any intact protein, (ii) is "gut-healing", that is, effective to heal damage already inflicted on the infant's digestive system, and (iii) yet meets the deliverability requirements specified. The problem is solved with a formula having a tailored distribution of amino acids and nucleotides which in combination with a source of unsaturated fats and relatively short chain carbohydrates and other ingredients, provide all the vitamin and mineral needs of the infant, yet prevent GI problems. A nucleotide consists of a nucleoside combined with phosphoric acid; a nucleoside is a compound made of a sugar and a purine or pyrimidine base, especially one obtained by hydrolysis of a nucleic acid, such as adenosine. The term "nucleotide" is used herein as an equivalent of "nucleoside" in that the form in which the compound is present is not critical so long as the specified number of "nucleotide equivalents" are used. A "nucleotide equivalent" refers to the nucleotide content present in any one or more of the following forms: ribo-nucleosides, ribo-nucleotides, RNA, phosphate esters and d-ribose adducts of one with another; the various forms of nucleotides are determined, calculated and expressed as the monophosphate esters.

Unless there is reason to suspect an infant will be allergic to mammalian milk, such as cow's milk, and/or to the protein in "soy milk", as for instance when an older sibling suffered from the allergy, a typical infant acquires cow's milk-induced enteropathy or enterocolitis, commonly referred to as "damaged gut", and becomes at-risk under several circumstances. The condition may be evident very soon if the infant is never breast-fed by its mother but is immediately fed an infant formula; the condition may be evident almost as quickly if the infant is breast-fed by its mother who drinks cow's milk or goat's milk; the condition may be evident a little later when the infant ceases to be breast-fed or the mother does not drink cow's milk, or does not drink sufficient cow's milk to impart evident signs of the condition in the infant; or the condition may be evident when the infant is breast-fed but not sufficiently well to provide all the infant's nutrition. Such evident signs of "damaged gut" include vomiting, diarrhea, and/or blood in the stool. A formula which fails to heal such damage is deemed deficient for the needs of an at-risk infant with damaged gut.

As will presently be evident, numerous infant-formulae purportedly especially formulated for infants and free of any milk-derived protein, fall far short of meeting the exigent requirements of a formula specifically directed to an infant in this particular mode of distress.

In particular, U.S. Pat. No. 5,719,133 teaches a dietary composition containing 100% free amino acids specially designed to provide a balance of amino acids for adolescents, but does not provide any nucleotides. Since the formula in the '133 patent addressed a different problem, namely one where an adolescent needed the protein content essentially free of intact protein, but was otherwise unrestricted with respect to nutrients able to provide nucleotides, the amino acids provide from 10% to 20% of the total caloric content of the formula; the lipid component provides from 20% to 35% of the total caloric content with no restriction as to its source; and the carbohydrate provides from 50% to 65% of the total caloric content with no restriction as to the chain length thereof. However, it should not be surprising that the ranges of both essential and non-essential amino acids disclosed, and the ratios of certain amino acids to others, which ranges and ratios are designed to balance the diet of an adolescent, are inappropriate for an at-risk infant. It is found that the optimum lipid content for an at-risk infant-formula provides 50% of the total caloric content, but to solubilize fat in powder form for specified deliverability required adjusting the distribution of amino acids and nucleotides. Moreover, the carbohydrate content of the '133 formula is too high, and the lipid content too low for a desirable formula for at-risk infants.

U.S. Pat. No. 5,066,500 to Gil et al teaches the use of any one or more of all nucleotides/nucleosides in a humanized milk formula for low-birth weight, premature and pre-term infants, teaches the use of cow's milk sometimes as powder milk, and "butterfat" in each example; and, for nitrogenous sources, teaches "a mixture of dairy proteins (casein or sodium and calcium caseinates and lactose free lactalbumin) and protein hydrolyzates with low molecular weight (maximum molecular weight 1,000 Daltons, average molecular weight, 500 Daltons). As carbohydrate sources, glucose polymers are employed, such as dextrinmaltose with a different grade of dextrose equivalent degree, preferably between 10 and 30 DE. Fats are employed as a mixture of animal and one or more vegetable fats to meet the essential fatty acids requirements of patients."(see col 9, lines 45–55). There is no suggestion that the protein be provided by only a combination of essential and non-essential amino acids, and none that there may be anything critical about the choice of a spectrum of amino acids and nucleotides, each in specified ranges, which are chosen to be absorbed and utilized by an at-risk infant.

U.S. Pat. No. 4,544,559 to Gil et al teaches the use of any one or more of all nucleotides/nucleosides in a humanized milk formula for infants which formula is manufactured as a sterilized fluid or an instant powdered milk. Both fluid and powder purportedly contain nucleotides AMP, CMP, GMP, IMP and UMP at concentrations similar to those found in human milk, and the remaining components are said to comply with the standards of EPSGAN and AAP. However, the required precise ratios (sic) claimed are as follows: AMP (adenosine-mono-phosphate) 1.7 mg/L; CMP (cytidine-monophosphate) 1.5 mg/L; GMP (guanosine-monophosphate) 1.9 mg/L, UMP (uridine-monophosphate) 4.4 mg/L; and IMP (inosine-monophosphate) 0.6 mg/L. Though it is unclear whether the "ratios" are based on 1 L of humanized milk in liquid form, or whether the 1 L basis includes all the nucleotides added, it is clear that as in the '500 patent, there is no suggestion that such a formula would meet the function of a complete nutritional support for an at-risk infant, or that specified ranges of nucleotides in combination with free L-Glutamine would allow damaged gut to heal and promote cell division for growth of the infant.

AU 200022638-A to Gil et al, assigned to Abbott Laboratories, discloses a nutritionally balanced nourishing product for preparation of infant formulas and dietetic products for adults which comprises adenosine and at least one other nucleoside. Whether fed to infants or adults, it is evidently essential that adenosine be present in combination with another nuecleoside irrespective of the remainder of the composition. But this is well known (see Gil et al European Patent No. 0302807 B1, May 1988). Then Gil et al disclose a range of guanosine/guanosine phosphate is from 3.32–0.27 mg/l 100 g, dry basis, which is far less than the concentration required in the at-risk infant formula (10.97–5.1 mg/100 g, dry basis); and the disclosed range of cytidine/cytidine phosphate is from 10.16–3.52 mg/100 g, dry basis, which is far less than the concentration required in the at-risk infant formula (21.9–10.97 mg/100 g, dry basis). Since the only amino acid stated to be present in the Gil et al infant formula is L-cystine, carnitine being an amino acid derivative syntesized from lysine and methionine, it is evident that the Gil et al infant's formula is not based on a combination of essential and non-essential amino acids. More importantly, Gil et al failed to recognize the importance of the concentration of free L-glutamine which should be in the range from 2–3 gm of free L-glutamine per 1000 cals.

Though one would be inclined to formulate an infant-formula in which each amino acid, whether "essential" or "non-essential", is present at the upper limit of the World Health Organization (WHO) and Life Sciences Research Office (LSRO) guidelines to ensure that the maximum amount of nutrition is delivered, such a formula is unlikely to meet the requirements of the Infant Formula Act (1980). It is noteworthy therefore that the relative amounts of nucleotides taught in the '559 formulae are even less than the amounts specified for the lower ranges of the amounts found in human milk (see Table 1 below). Moreover, it is found that a formula with the relative amounts of nucleotides specified near the high end of the ranges in human milk would lack desired absorption and utilization by an at-risk infant, and also lack the specified deliverability. References teaching that each and every nucleotide may be used in a wide range of more than an order of magnitude (that is, the higher limit is more than 10 times greater than the lower limit) fail to enable one to choose the amount of a nucleotide which will be assimilated and utilized, do not suggest what the effect of high relative concentrations of particular nucleotides may be on the damaged gut of an at-risk infant, and provide no indication of the deliverability of a particular combination of amino acids and nucleotides irrespective of the other components of the infant-formula.

The inadequacy of the prior art resulted in having to choose not only the distribution of specific nucleotides but also that of individual essential and non-essential amino acids in the novel formula for an at-risk infant. The choice resulted in a different distribution compared to those used in the formula for a baby older than one year. In this regard it should be noted that "essential" and "non-essential" amino acids are equally important in a healthy metabolic process, and the effect of omitting even a single amino acid from either category in an infant's diet would result in failure of the infant's body to use all other amino acids except as an energy source. Non-essential amino acids can be synthesized in the body, therefore need not be provided in the diet. Particularly because there are no WHO or LSRO guidelines for the distribution of non-essential amino acids, and the guideline for nucleotides is their concentration in human milk, much responsibility for an at-risk infant's health is assumed when the distribution of amino acids, both essential and non-essential, is decided upon, though as a practical matter, a formula for an at-risk infant cannot be marketed for general use without the recipe falling within parameters set by both the WHO and LSRO.

Though each nucleotide may be used in a wide range found to be present in human milk, and it would be logical to use each nucleotide in an amount near the upper limit of its allowable range to ensure that the maximum amount of nucleotide is available to the infant, it has been found undesirable to do so. From the ranges of nucleotide equivalents present in human milk, set forth in Table 1 below, and the use in commercial infant-formulae of much lower amounts of each nucleotide than the allowable upper limit, it is evident that numerous considerations come to bear on a choice of the proportions in which the nucleotides are used relative to each other.

TABLE 1*

| Nucleotide | Range in which present in human milk, mg/L |
|---|---|
| Adenosine (AMP) | 3.5–25.9 |
| Guanosine (GMP) | 5.4–26 |
| Cytidine (CMP) | 8–35.2 |
| Uridine (UMP) | 5.1–16.3 |

*see Leach, J. L. et al, Table 2, AJCN 1995:1224–1230
Inosine (IMP) in an amount <100 ppm is also generally present.

With respect to enriching an at-risk infant's formula with nucleotides, there are currently available the following commercial brands: ENFAMIL infant formula, SIMILAC infant formula and private label infant formula manufactured by Wyeth (formerly known as SMA) but each is a milk-based formula unsuitable for an at-risk infant. In each of the marketed formulae is added a combination of particular vitamins, minerals, trace elements, etc., to supplement the diet provided by each infant-formula to satisfy as completely as possible, the needs of the infant, and avoid undue risk of undetected deficiencies.

SUMMARY OF THE INVENTION

It has been discovered that a non-milk based hypoallergenic infant-formula may be formulated to deliver no more than about 240 calories per 240 ml (8 fl oz) serving with about 50% of the calories derived from unsaturated fats and fatty acids, about 39% from carbohydrates, the remaining from free amino acids, it being essential that the formula is combined with nucleotides, essentially free of inosine, present in an amount in the range from 40 to 60 mg per liter of ready-to-feed infant formula, preferably about 76 mg of a specified distribution of nucleotides per 1000 calories of total caloric content, in combination with from 2–3 gm of free L-Glutamine per 1000 cals, so as to have a renal solute load of less than 200 mOsm/liter, all ingredients in a powder having a primary particle size such that more than 85% of the particles are smaller than 180 $\mu$m, that is, pass through a No. 80 sieve, U.S. Standard Test Sieves (Wire Cloth), and which is deliverable as specified as a liquid having a viscosity less than 10 cp at 25° C.

It is therefore a specific object of this invention to provide a non-milk based formula essentially free of protein hydrolysate, for an infant no more than one year old, afflicted with CMA and/or an allergy to the protein in "soy milk", and/or digestive or absorption problems; the novel combination of key ingredients of the formula consists essentially of (i) a critically high amount of essential vegetable fats as triglycerides derived from relatively long C12 to C20 chain fatty acids, which fats have a caloric content in the range from 48–52%, most preferably 50%, of the total caloric content of the formula; (ii) relatively short chain length carbohydrates contributing less than 40% of total calories; and (iii) free amino acids including about 2–3 gm of free L-Glutamine/1000 cals, contributing the remainder of the caloric content; this level of glutamine is similar to the amount in human milk; the ability of an at-risk infant to utilize higher levels than 3 gm/l 1000 cals has not been extensively studied.

The novel dietary composition is required to be formulated as a powder with other ingredients adapted to provide storage stability and specified deliverability. Preferably the combined free amino acids provide from 10–12%, most preferably 11% of total calories, and the carbohydrate provides from 37–41%, most preferably 39% of total calories; the foregoing triglyceride-rich combination is then enriched with a chosen proportion of nucleotide equivalents for each nucleotide substantially to mimic the amounts present in human milk, preferably in the range from about 45–55 mg of combined nucleotides per liter. The proportions of amino acids and nucleotides in combination is chosen so as to provide a powder in which all amino acids and nucleotides are soluble and deliverable as specified.

It is another specific object of this invention to provide a palatable elemental formula having flavor desirable for an at-risk infant, and organoleptic properties and mothfeel patterned after human milk, provided osmolality at standard dilution (0.67 cal/ml), is maintained below 300 mOsm/Kg water, so as to effect in combination with the stated concentration of free L-Glutamine, healing of the infant's damaged gut, and further provided the formula is enriched with a distribution of nucleotides essentially free of inosine, which formula is a nutritionally complete yet storable as a powder and deliverable as specified.

It is still another specific object of this invention to provide the above-described fats as relatively long chain triglycerides having in excess of 40 carbon atoms formed with fatty acids having in the range from C12 to C20 carbon atoms, which fats are unexpectedly highly assimilable by an infant in the absence of casein hydrolysate, yet the novel formula has specified deliverability because the combination of fatty acids used are easily solubilized without clumping so as not to clog the orifice in a nipple on a bottle.

A method is provided for nourishing an at-risk infant by feeding it with the above-described infant-formula which provides complete nutrition, promotes cell division for normal growth and allows the infant's damaged gut to heal.

DETAILED DESCRIPTION OF A PREFERRED EMBODIMENT

When a powder infant-formula is shaken with water, appreciable amounts of minerals and vitamins, vitally important in the formula, remain in suspension after 30 secs, and coupled with carbohydrates, fats and free amino acids, often have a tendency to block the orifice in a nipple on a feeding bottle. This tendency is exaggerated when the formula contains enough fatty acids to provide about 50% of the total caloric content of the infant-formula. Fat globules are not readily solubilized in liquid formula which upon standing, tends to allow fat globules to harden and clog a feeding tube or the orifice of a nipple.

Though the foregoing problem would be solved by using triglycerides formed with medium chain fatty acids having in the range from C8 to C12 carbon atoms, such fatty acids fail to provide the required essential fats for an at-risk infant. An infant's diet, deficient in essential fats, causes overall growth retardation, sparse hair growth, poor wound healing, increased susceptibility to infection and dry, flaky skin. Quite unexpectedly, choosing a mixture of longer chain triglycerides having in excess of 40 carbons per molecule, formed with fatty acids having in the range from C12 to C20 carbon atoms, in combination with free amino acids, allows the longer chain triglycerides to be assimilated, thus providing the critical essential fatty acids, so long as the distribution of those fats chosen can be efficiently utilized by an infant. In the novel infant-formula the following combination of triglycerides formed from fatty acids having chain lengths in the range from C12 to C20, each triglyceride present in a range from at least 10% to 15% of the total amount of triglycerides, is found to be highly effective. Most effective is a combination of palm olein (45%), soy (20%), coconut (20%), and high oleic sunflower (15%). Though a very small amount of a free fatty acid is tolerable, it is preferred that the formula be essentially free of free fatty acids. By "essentially free" is meant that the amount present is one percent (1%) or less by weight of the infant formula.

For reasons particular to the requirements for each commercially available infant-formula, the distribution of the nucleotides in known infant-formulae is either too broadly specified to be useful, or when usefully defined, the distributions are different in each known formula with little regard to teaching the criticality of the amounts of particular nucleotides disclosed. The criticality of the amounts of particular nucleotides in the ranges in a specific case used is dictated in large part by the age of the child to be treated, and the specific treatment the child requires. Such criticality is emphasized in the diet of an at-risk infant, because in the ranges used, (i) the nucleotides must not only provide the entire usable amounts of each nucleotide but also (ii) are required to help heal an infant's damaged gut. The choice of amounts of each ingredient must then be tailored to provide the formula in powder form, without adversely affecting the specified deliverability. The distribution of each nucleotide in specific prior art infant-formulae, each in its most preferred form (for which the concentrations of ingredients are duplicated from advertised commercial embodiments) is set forth in Table 2 below, as mg/L (mg of nucleotide equivalents per liter of infant formula), for comparison with the novel infant-formula:

TABLE 2

| Nucleotide | At-risk Infant Formula | Enfamil | Wyeth Private | Similac |
|---|---|---|---|---|
| Adenosine | 7 | 5 | 4 | 11 |
| Guanosine | 10 | 4 | 2 | 15 |
| Cytidine | 22 | 11 | 16.5 | 30 |
| Uridine | 11 | 6 | 5 | 16 |
| Inosine | 0 | 0 | 2 | 0 |
| Total | 50 | 26 | 29.5 | 72 |

None of the prior art distributions of nucleotides recognized the significance of the ratio of the total nucleotide equivalents to the amount (gm) of free L-Glutamine (0.22 g/100 Kcal in the best mode) present, which ratio in the novel formula is in the range from 25 to 45, preferably from 30 to 40. Moreover, it is presently believed that, despite the wide range within which each nucleotide is present in human milk, and particularly the wide range of adenosine therein, it is essential, for maximum benefit, to provide at least 5 mg/L (mg of nucleotide equivalents per liter of infant formula) of each nucleotide but limit the total amount of nucleotides to an amount in the range from about 45–55 mg/L, and also limit the amount of adenosine relative to the other combined nucleotides so that the ratio of (total nucleotides including adenosine): (adenosine) is at least 6, ratios lower than 6 indicating more adenosine than is desirable.

Provided the foregoing limitations with respect to the ratios are adhered to, each of the following four nucleotides may be used in the ranges given below:
Adenosine 5–10 mg/L; Guanosine 7–15 mg/L;
Cytidine 15–30 mg/L; and Uridine 8–16 mg/L.

The stated proportion of nucleotides in combination with the stated proportion of free amino acids, particularly including required free L-Glutamine, in the at-risk infant-formula is found to promote better growth of beneficial bacteria than a combination of casein (derived from milk) and the same proportions of nucleotides. Better growth of beneficial bacteria promotes a healthier intestinal tract which is protected against infection, resulting in efficient utilization of nutrients ingested by the infant.

Though the amount of free L-Glutamine is relatively low in comparison to the amount of essential fats and carbohydrate, it is critical that at least from 2–2.5 gm of free L-Glutamine be used for 1000 cals of formula, because in this range, it is particularly beneficial for cell division during the infant's growth, but at higher levels than 3 gm/1000 cals is deemed difficult for an at-risk infant to utilize. Choosing the appropriate amount of L-Glutamine to be added is difficult because neither WHO nor LSRO guidelines specify what levels are to be used, on the assumption that most infants have a normal digestive system. Moreover, though L-Glutamine and glutamic acid are interconvertible for nutrition in a normal healthy adolescent, free L-Glutamine cannot be substituted with glutamic acid which does not work in the gut of an at-risk infant in a manner analogous to L-Glutamine. Recognizing the importance of glutamine, known infant formulae incorporate it as bound glutamine in part of a peptide chain of an intact protein. This requires an infant to hydrolyze the protein. Because L-glutamine is unstable in aqueous liquid, free L-Glutamine is contraindicated in a storable liquid infant formula. To provide stability of a dry powder formula which is to be diluted with water, dry L-glutamine is added in the formulated powder. Most preferably, the free L-Glutamine is combined with a minor amount of glutamic acid so that together they provide from 14 to 16 gm per 100 gm of amino acids present.

The amino acid component of the nutrient powder of this invention provides from 10 to 12%, most preferably about 11% of the total caloric content of the powder. The amino acid component consists essentially of the following essential amino acids used in the ranges indicated: 3.0 to 4% L-histidine, 5 to 7% L-isoleucine (branched chain), 10 to 11% L-leucine (branched chain), 7.5 to 8.5 % L-lysine, 1.5 to 2.5% L-methionine, 5 to 6% L-phenylalanine, 4 to 5% L-threonine, 1.5 to 2% L-tryptophan, and 6.0 to 7.0% L-valine (branched chain); and, also the following non-essential amino acids: 3.5 to 4.5% L-alanine, 5.5 to 6.5% L-arginine, 5.5 to 6.5% L-aspartic acid, 2 to 3% L-cystine, 7 to 9% L-glutamine, 6 to 8% L-glutamic acid, 1.5 to 2.5% glycine, 7.5 to 9.0% L-proline, 5 to 6% L-serine, and 3 to 5% L-tyrosine, all based on total weight of said amino acid component.

Most preferably, in the best mode, the amino acid component consists essentially of the following specific amounts of essential amino acids 3.1% L-histidine, 5.8% L-isoleucine, 10.3% L-leucine, 7.9% L-lysine, 1.9% L-methionine, 5.5% L-phenylalanine, 4.5% L-threonine, 1.7% L-tryptophan, and 6.5% L-valine; and, the following specific amounts of non-essential amino acids: 4.0% L-alanine, 6.0% L-arginine, 5.9% L-aspartic acid, 2.3% L-cystine, 7.9% L-glutamine, 7.2 L-glutamic acid, 1.8% glycine, 8.3% L-proline, 5.4% L-serine, and 4.0% L-tyrosine.

The combined essential and non-essential amino acids most preferably consist essentially of the foregoing amino acids in the range from 10% to 15% by weight of the nutrient powder, the non-essential amino acids being present in a major proportion by weight relative to the essential amino acids. More importantly, in view of the beneficial effect of a relatively high amount of both L-Arginine and branched chain essential amino acids on the liver functions of an at-risk infant, it is most preferred that in the novel formula, the ratio of each of the individual branched chain essential amino acids (L-Leucine, L-Lysine and L-Valine) to L-arginine be less than 2; and that the ratio of the total weight of branched chain essential amino acids to L-Arginine be in the range from 4 to 5.

The amino acid profile of the novel formula for an at-risk infant is distinct from one disclosed in the '133 patent, for an adolescent. The relative amounts of individual amino acids based on the total weight of amino acids in a preferred novel infant-formula and the '133 formula are set forth side-by-side in Table 3 below, as "% by weight", separated as essential and non-essential amino acids.

TABLE 3

| Comparison of Essential Amino Acid Profiles, % by weight | | |
|---|---|---|
| Essential Amino Acid | the '133 formula | infant-formula |
| L-histidine | 2.3–2.8 | 2.9–3.3 |
| L-isoleucine | 6.1–7.4 | 5.5–6.0 |

TABLE 3-continued

Comparison of Essential Amino Acid Profiles, % by weight

| Essential Amino Acid | the '133 formula | infant-formula |
|---|---|---|
| L-leucine | 8.5–10.2 | 10.0–10.6 |
| L-lysine | 6.6–8.0 | 7.6–8.2 |
| L-methionine | 3.1–3.8 | 1.6–2.2 |
| L-phenylalanine | 5.5–6.6 | 5.2–5.8 |
| L-threonine | 4.8–5.8 | 4.1–4.8 |
| L-tryptophan | 1.7–2.1 | 1.4–2.0 |
| L-valine | 7.0–8.4 | 6.2–6.8 |

TABLE 4

Comparison of Non-Essential Amino Acid Profiles, % by weight

| Essential Amino Acid | the '133 formula | infant-formula |
|---|---|---|
| L-alanine | 5.7–6.9 | 3.7–4.3 |
| L-arginine | 6.2–7.5 | 5.7–6.3 |
| L-aspartic acid | 5.9–7.1 | 5.6–6.2 |
| L-cystine | 2.3–2.8 | 2.0–2.6 |
| L-glutamine | 12.9–15.5 | 7.6–8.2 |
| L-glutamic acid | 3.8–4.6 | 6.9–7.5 |
| glycine | 3.2–3.9 | 1.5–2.1 |
| L-proline | 5.0–6.0 | 8.0–8.6 |
| L-serine | 5.4–6.5 | 5.1–5.7 |
| L-tyrosine | 4.0–4.8 | 3.7–4.3 |

The required solid powder form of the novel formula preferably has a caloric content from about 4–5 cal/gm, and when 32.6 gm is diluted with water for an individual 240 ml (8 fl oz) feeding, the liquid has a caloric content of about 160 cals (0.67 cal/ml or 20 cal/fl oz) and an osmolality less than 300 mOsm/Kg of water, most preferably about 290 mOsm/Kg. The powder is storable in a sealed container for a period in the range from about 1 to 2 years at about 20° C. (room temperature) and 100% humidity.

Unless an at-risk infant is unable to ingest the solubilized powder orally, the liquid is administered enterally. If administered orally the liquid is preferably flavored and served cold, providing complete nutrition in the range of from about 160–240 cals/8 fl oz (240 ml) feeding, when the minimum daily caloric intake required based on a RDI (recommended daily intake), is provided. The RDI is calculated as (infant's weight in kg) multiplied by 117 cals. For infants weighing 2.3 kg (5 lb) and 11.5 kg (25 lb), a caloric intake in the range from about 269 calories to 1346 per day, respectively has a beneficial effect with respect to healing gut damage evidenced by inflammatory bowel disease, intractable diarrhea, lactose intolerance, short bowel syndrome, cystic fibrosis, cow's milk protein enteropathy or sensitivity, pre or post surgery, trauma, AIDS, malabsorption syndrome, gastroenteritis, GI fistula, and pancreatic disorder.

The liquid may be administered enterally in the range from about 0.67 to 1.0 calorie per ml dilution, preferably 0.67 cal/ml dilution, via a nasogastric, nasointestinal, esophagostomy, gastrostomy, or jejunostomy feeding tube, preferably at room temperature, by continuous drip technique, or using a suitable infusion pump. Because of the liquid's homogeneity and low viscosity, small bore feeding tubes (16 gauge catheter or #5 French tube) may be used to optimize tolerance. To ensure delivery of a normal daily fluid requirement, additional fluids may be included to maintain hydration and adequate urine output.

The following illustrative example in which the ingredients are listed with the value of each per 100 cals of formula, provides the best mode of the novel formula:

| Free amino acids, gm | 2.75 |
|---|---|
| Triglycerides, gm | 5.6 |
| Nucleotides, mg | 7.5 |
| Linoleic acid, mg | 963 |
| Vitamin A, IU | 400[1] |
| Vitamin D, IU | 80 |
| Vitamin E, IU | 3[2] |
| Vitamin K, mcg | 15 |
| Thiamine, mcg | 90 |
| Riboflavin | 130 |
| Vitamin $B_6$, mcg | 120[3] |
| Vitamin $B_{12}$, mcg | 0.4 |
| Niacin, mcg | 1500 |
| Folic acid, mcg | 15 |
| Pantothenic acid, mcg | 700 |
| Biotin, mcg | 4 |
| Vitamin C, mcg | 12 |
| Choline, mg | 13 |
| m-Inosotol, mg | 20 |
| Calcium, mg | 91[4] |
| Phosphorus, mg | 70[4] |
| Magnesium, mg | 12 |
| Iron, mg | 1.65 |
| Zinc, mg | 1.0 |
| Manganese, mg | 80 |
| Copper, mcg | 120 |
| Iodine, mcg | 15 |
| Sodium, mg | 50 |
| Potassium, mg | 110 |
| Chloride, mg | 80 |
| Selenium, mcg | 2.7 |
| Chromium, mcg | 3.2 |
| Molybdenum, mcg | 2.9 |
| Carnitine, mg | 2.0 |
| Taurine, mg | 6.0 |

[1] = no (beta) β-carotene
[2] = (alpha) α-tocopherol: linoleic acid about 3 IUs: 1 gm
[3] = $B_6$: free amino acid ratio about 40 mcg: 1 gm
[4] = calcium: phosphorus about 1.3:1

Tests currently in progress indicate that it is critical that free L-Glutamine be present in an amount sufficient to re-establish growth of an enterocyte layer of cells on the luminal side of the small intestine, and in a major amount relative to glutamic acid so that the ratio of free L-Glutamine to glutamic acid is greater than 1, and the total L-glutamine and glutamic acid is less than 16 gm/100 gm of amino acids.

We claim:

1. A nutrient powder for an infant-formula providing a complete source of nutrition for an at-risk infant no more than one year old, said powder comprising,
   (a) a carbohydrate component providing from 37 to 41% of total caloric content of said powder;
   (b) a lipid component derived from unsaturated vegetable oils providing from 48 to 52% of total caloric content of said powder;
   (c) an amino acid component providing from 10 to 12% of the total caloric content of said powder in combination with from 2–3 gm of free L-Glutamine per 1000 cals provided by said powder so as to have a renal solute load of less than 200 mOsm/L; and,
   (d) nucleotides, essentially free of inosine, present in an amount in the range from 40 to 60 mg per liter of ready-to-feed infant formula;
   wherein,
      all ingredients in said powder have a primary particle size such that more than 85% of the particles are smaller than 180 μm, and said powder is deliverable within less than 30 secs as a liquid having a viscosity less than 10 cp at 25° C. when a unit dosage amount of 32.6 gm of said powder is manually shaken with water at 35° C. in a bottle containing 240 ml (8 fl oz) of water.

2. The nutrient powder of claim 1 wherein said unsaturated vegetable oils consist essentially of a mixture of longer chain triglycerides having in excess of 40 carbons per molecule, said triglycerides being derived from fatty acids having in the range from C12 to C20 carbon atoms and each triglyceride be present in a range from at least 10% to 15% of the total amount of triglycerides.

3. The nutrient powder of claim 2 wherein said triglycerides are present in the following amounts: palm olein, 45%; soy, 20%; coconut, 20%; and high oleic sunflower, 15%.

4. The nutrient powder of claim 2 wherein said nucleotides are present in the following ranges: Adenosine 5–10 mg/L; Guanosine 7–15 mg/L; Cytidine 15–30 mg/L; and Uridine 8–16 mg/L; and in an amount such that the ratio of (total nucleotide equivalents): (the amount of free L-Glutamine) is in the range from 25 to 45.

5. The nutrient powder of claim 2 wherein said amino acid component consists essentially of the following essential amino acids: 3.0 to 4% L-histidine, 5 to 7% L-isoleucine, 10 to 11% L-leucine, 7.5 to 8.5% L-lysine, 1.5 to 2.5% L-methionine, 5 to 6% L-phenylalanine, 4 to 5% L-threonine, 1.5 to 2% L-tryptophan, and 6.0 to 7.0% L-valine; and, the following non-essential amino acids: 3.5 to 4.5% L-alanine, 5.5 to 6.5% L-arginine, 5.5 to 6.5% L-aspartic acid, 2 to 3% L-cystine, 7 to 9% L-glutamine, 6 to 8% L-glutamic acid, 1.5 to 2.5% glycine, 7.5 to 9.0% L-proline, 5 to 6% L-serine, and 3 to 5% L-tyrosine, all based on total weight of said amino acid component.

6. The nutrient powder of claim 5 wherein said non-essential amino acids are present in a major proportion by weight relative to the essential amino acids, and the amount of free L-glutamine is in the range from 7–9 g/100 g of total amino acids.

7. The nutrient powder of claim 6 wherein the ratio of each of branched chain essential amino acids L-Leucine, L-Lysine and L-Valine to L-Arginine is less than 2; and that the ratio of the total weight of branched chain essential amino acids to L-Arginine is in the range from 4 to 5.

8. A method of nourishing an at-risk infant which comprises feeding the infant with a liquid prepared from a nutrient powder comprising:

(a) a carbohydrate component providing from 37 to 41% of total caloric content of said powder;

(b) a lipid component derived from unsaturated vegetable oils providing from 48 to 52% of total caloric content of said powder;

(c) an amino acid component providing from 10 to 12% of the total caloric content of said powder in combination with from 2–3 gm of free L-Glutamine per 1000 cals provided by said powder so as to have a renal solute load of less than 200 mOsm/L; and, (d) nucleotides, essentially free of inosine, present in an amount in the range from 40 to 60 mg per liter of ready-to-feed infant formula;

wherein,
all ingredients in said powder have a primary particle size such that more than 85% of the particles are smaller than 180 μm, and said powder is deliverable within less than 30 secs as a liquid having a viscosity less than 10 cp at 25° C. when a unit dosage amount of 32.6 gm of said powder is manually shaken with water at 35° C. in a bottle containing 240 ml (8 fl oz) of water.

9. The method of claim 8 wherein said unsaturated vegetable oils consist essentially of a mixture of longer chain triglycerides having in excess of 40 carbons per molecule, said triglycerides being derived from fatty acids having in the range from C12 to C20 carbon atoms and each triglyceride be present in a range from at least 10% to 15% of the total amount of triglycerides.

10. The method of claim 9 wherein said triglycerides are present in the following amounts: palm olein, 45%; soy, 20%; coconut, 20%; and high oleic sunflower, 15%.

11. The method of claim 9 wherein said nucleotides are present in the following ranges: Adenosine 5–10 mg/L; Guanosine 7–15 mg/L; Cytidine 15–30 mg/L; and Uridine 8–16 mg/L; and in an amount such that the ratio of (total nucleotide equivalents) : (the amount of free L-Glutamine) is in the range from 25 to 45.

12. The method of claim 9 wherein said amino acid component consists essentially of the following essential amino acids: 3.0 to 4% L-histidine, 5 to 7% L-isoleucine, 10 to 11% L-leucine, 7.5 to 8.5% L-lysine, 1.5 to 2.5% L-methionine, 5 to 6% L-phenylalanine, 4 to 5% L-threonine, 1.5 to 2% L-tryptophan, and 6.0 to 7.0% L-valine; and, the following non-essential amino acids: 3.5 to 4.5% L-alanine, 5.5 to 6.5% L-arginine, 5.5 to 6.5% L-aspartic acid, 2 to 3% L-cystine, 7 to 9% L-glutamine, 6 to 8% L-glutamic acid, 1.5 to 2.5% glycine, 7.5 to 9.0% L-proline, 5 to 6% L-serine, and 3 to 5% L-tyrosine, all based on total weight of said amino acid component.

13. The method of claim 12 wherein said non-essential amino acids are present in a major proportion by weight relative to the essential amino acids.

14. The method of claim 13 wherein the ratio of each of branched chain essential amino acids L-Leucine, L-Lysine and L-Valine to L-Arginine is less than 2; and that the ratio of the total weight of branched chain essential amino acids to L-Arginine is in the range from 4 to 5.

* * * * *